US012667257B2

(12) United States Patent
Chikkatur et al.

(10) Patent No.: US 12,667,257 B2
(45) Date of Patent: Jun. 30, 2026

(54) SYSTEM AND METHOD FOR RETINAL IMAGING

(71) Applicant: Forus Health Pvt Ltd., Bengaluru (IN)

(72) Inventors: Harshitha Prakash Chikkatur, Bengaluru (IN); Venkatakrishnan Srinivasan, Bengaluru (IN); Midhula Vijayan, Bengaluru (IN); Deepthi Keshav Prasad, Bengaluru (IN)

(73) Assignee: FORUS HEALTH PVT LTD., Bengalurn (IN)

( * ) Notice: Subject to any disclaimer, the term of this patent is extended or adjusted under 35 U.S.C. 154(b) by 300 days.

(21) Appl. No.: 18/379,345

(22) Filed: Oct. 12, 2023

(65) Prior Publication Data

US 2024/0122474 A1    Apr. 18, 2024

(30) Foreign Application Priority Data

Oct. 13, 2022    (IN) .............................. 202241058544

(51) Int. Cl.
    *A61B 3/14*        (2006.01)
    *A61B 3/00*        (2006.01)
    (Continued)

(52) U.S. Cl.
    CPC ............ *A61B 3/145* (2013.01); *A61B 3/0008* (2013.01); *A61B 3/0025* (2013.01); *A61B 3/0058* (2013.01); *A61B 3/0091* (2013.01); *A61B 3/1208* (2013.01); *A61B 3/185* (2013.01); *A61B 2560/0431* (2013.01); *A61B 2560/0462* (2013.01); *A61B 2562/0219* (2013.01)

(58) Field of Classification Search
    CPC ..... A61B 3/145; A61B 3/0008; A61B 3/0025; A61B 3/0058; A61B 3/0091; A61B 3/1208; A61B 3/185; A61B 2560/0431; A61B 2560/0462; A61B 2562/0219; A61B 3/0041; A61B 3/14; A61B 3/00; A61B 3/12; A61B 3/18
USPC .................................................. 359/206–211
See application file for complete search history.

(56) References Cited

U.S. PATENT DOCUMENTS

| | | | |
|---|---|---|---|
| 9,289,122 B2 | 3/2016 | Chinnock et al. | |
| 2013/0033593 A1* | 2/2013 | Chinnock ................ | A61B 3/14 |
| | | | 348/78 |
| 2021/0110616 A1* | 4/2021 | Watola ................. | G09B 21/008 |

FOREIGN PATENT DOCUMENTS

WO        2022066429 A1    3/2022

OTHER PUBLICATIONS

Indian Office Action 202241058544, Issued Nov. 29, 2023.

* cited by examiner

*Primary Examiner* — Thomas K Pham
*Assistant Examiner* — Kuei-Jen L Edenfield
(74) *Attorney, Agent, or Firm* — The Belles Group, P.C.

(57) ABSTRACT

Disclosed is a system for retinal imaging. The type of image to be captured is selected by a user. Corresponding fixation stimulus is displayed on a fixation screen of the disclosed device for the subject to fix their gaze on. The device comprises illumination sources and, illumination optics and imaging optics, a 3-D accelerometer, and a camera. Signal from the 3-D accelerometer, and the video of the eye of the subject captured by camera are used by a computing device that uses AI techniques to vary the position of the fixation stimulus to obtain a stabilized image of the eye of the subject. The position of the fixation stimulus is varied to compensate for the movement of the handheld device to obtain a stabilized retinal image. Once stabilized, the image is captured.

6 Claims, 7 Drawing Sheets

(51) Int. Cl.
*A61B 3/12*          (2006.01)
*A61B 3/18*          (2006.01)

300

700

SYSTEM AND METHOD FOR RETINAL IMAGING

CROSS-REFERENCE TO RELATED PATENT APPLICATIONS

The present application claims priority to Indian Patent Application No. 202241058544, filed on Oct. 13, 2022. The disclosure of the aforementioned priority application is incorporated herein by reference in its entirety.

FIELD OF THE INVENTION

The present invention relates to the field of ophthalmic imaging systems and particularly to systems for retinal imaging, the system having a handheld imaging device.

BACKGROUND TO THE INVENTION

Retinal imaging devices are used to capture images of the retina of the eye of a subject. Such images are used to assess the medical or ophthalmological status of the subject's retina.

Normally, the retinal imaging device is placed in front of the subject's eye and the subject is asked to fix the gaze at a predetermined point in the space in front of the subject. When the subject's gaze is fixed on the point, an image is captured with an imaging device.

The point in space is determined by the type of image needed by the user. Examples of the types of images are macula centered image and optic disc centered image, as shown in FIGS. 1a and 1b, respectively. The word 'user' refers to, hereinafter in this disclosure, a person capturing the image and may be an operator of the imaging device, an ophthalmologist, a medical professional, and so on.

While handheld retinal imaging devices have certain advantages over fixed or tabletop devices, they are prone to unwanted movement due to the movement of both the subject's eye and the user's hand that is holding the device. Thus, the device may move to a different position in two dimensional and three-dimensional space ((X, Y) and (X, Y, Z), as known in the Cartesian coordinate system), other than the one from which a useful image of the region of interest can be captured while attempting to capture the retinal image of a subject's eye.

Images captured under such conditions may suffer from; a) undesired position of the retina in the image captured, b) blurred and hence unusable images, c) or both. One example of undesired position of the retina in the image is, obtaining a macula centered image while requiring an optic disc centered image.

Methods or means known in the art for obtaining a required image without the errors mentioned above are as follows.

Optical Image Stabilization (OIS), wherein motors are used to stabilize the position of either the lens or the image sensor within the imaging device. The drawback of this method is that it needs complicated arrangement of motors and constant calibration to achieve stabilization.

Digital Image Stabilization or Electronic Image Stabilization (DIS or EIS) wherein the peripheral regions of the captured image are cropped to provide a zoomed in view by using the peripheral area to adjust the stabilization.

Post-processing the captured images to get a clear image. This method is known as stabilization filter.

Another method used is to shift the image within the image sensor itself—a charge coupled device (CCD), for example—while the image is being captured based on an analysis of the apparent motion of bright stars. This method is used for imaging devices used for astronomical purposes. This is called Orthogonal Transfer CCD or OTCCD.

Mechanically stabilizing the imaging device using a harness and gimbal is also known. This is called Mechanical Image Stabilization (MIS)—sold under the brand name Steadicam®.

These methods suffer from one or more of: a) not being applicable to a retinal imaging device (OTCCD), b) being heavy and expensive (Steadicam), and c) unable to provide the required image with the required quality (DIS or EIS and stabilization filter).

SUMMARY OF THE INVENTION

Thus, there has been a need for a device and a method that can overcome or mitigate one or more of the above said inadequacies in the prior art.

Disclosed herein is a system for capturing a stabilized retinal image of an eye of a subject by a handheld retinal imaging device. The system comprises a handheld retinal imaging device and an. The external computing device is configured for receiving a user selection from a user, the user selection comprising a type of image to be captured, conveying data on an initial position of a fixation stimulus on a fixation screen based on a user selection, receiving video data of the eye of the subject from a camera and position data from a 3-D accelerometer and displaying a video based on the video data received from the camera, calculating a new position for the fixation stimulus on the fixation screen, based on one or more of, the user selection, the video data received from the camera and the position data received from the 3-D accelerometer, analyzing one or more frames of the video for determining, using artificial intelligence techniques, a stable image of the eye of the subject, on sensing a stabilized image, conveying a trigger to a light source of the handheld retinal imaging device for illuminating the eye of the subject and conveying a trigger to the camera for capturing a stabilized retinal image, illuminated by a light source.

Also disclosed is a handheld retinal imaging device that comprises an infrared light source for illuminating the eye of the subject, through illuminating optics configured for illuminating the eye of the subject, a source of visible light for illuminating the eye of the subject, through the illuminating optics, for a predefined duration, based on a trigger received from the external computing device, the fixation screen configured for displaying the fixation stimulus for the subject to gaze at during the use of the device, the position of the fixation stimulus on the fixation screen being based on an input received from the external computing device, and the 3-D accelerometer for sensing data corresponding to a movement of the handheld device and conveying it to the external computing device, and a camera configured for capturing video data of the eye of the subject and conveying the video data to the external device and capturing the retinal image of the eye of the subject, based on a trigger received from the external computing device and conveying retinal image data to the external computing device.

Also disclosed is a method for capturing a stabilized retinal image of an eye of subject using a handheld retinal imaging device, the method comprising steps of (a) a step of receiving by a computing device a user input on the type of image to be captured, (b) a step of conveying, by the computing device, data to a fixation screen on a position of a fixation stimulus on the fixation screen, (c) a step of receiving, by the computing device, video data of the eye of the subject from a camera of the handheld retinal imaging device, and data on a position of the handheld retinal imaging device, from a 3-D accelerometer of the handheld retinal imaging device, and displaying a video based on the video data provided by the camera, (d) a step of calculating, by the computing device, a new position for the fixation stimulus on the fixation screen, (e) a step of analyzing, by the computing device, one or more frames of the video data for determining, using artificial intelligence techniques, a stable image of the eye of the subject, (f) repeating steps c, d, and e until sensing, by the computing device, a stabilized image, (g) a step of conveying, by the computing device, a trigger to a light source to illuminate the eye of the subject and conveying a trigger to the camera for capturing a stabilized still retinal image, illuminated by the light source, and (h) a step of displaying, by the computing device, the stabilized still retinal image on a display device and storing still image data in a memory of the computing device.

To further clarify the advantages and features of the present invention, a more particular description of the invention will be rendered by reference to specific embodiments thereof, which is illustrated in the appended figures. It is to be appreciated, that these figures depict only typical embodiments of the invention and are therefore not to be considered limiting. The invention will be described and explained with additional specificity and detail with the accompanying figures hereinafter.

Further, persons skilled in the art to which this disclosure belongs will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those of ordinary skill in the art having the benefit of the description herein.

DESCRIPTION OF THE INVENTION

To promote an understanding of the principles of the disclosure, reference will now be made to the embodiment illustrated in the figures and specific language will be used to describe them. It will nevertheless be understood that no limitation of the scope of the disclosure is thereby intended. Such alterations and further modifications to the disclosure, and such further applications of the principles of the disclosure as described herein being contemplated as would normally occur to one skilled in the art to which the disclosure relates are deemed to be a part of this disclosure.

It will be understood by those skilled in the art that the foregoing general description and the following detailed description are exemplary and explanatory of the disclosure and are not intended to be restrictive thereof.

The terms "comprises", "comprising", or any other variations thereof, are intended to cover a non-exclusive inclusion, such that a process or method that comprises a list of steps does not include only those steps but may include other steps not expressly listed or inherent to such a process or a method. Similarly, one or more devices or sub-systems or elements or structures or components preceded by "comprises . . . a" does not, without more constraints, preclude the existence of other devices, other sub-systems, other elements, other structures, other components, additional devices, additional sub-systems, additional elements, additional structures, or additional components. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this disclosure belongs. The system, methods, and examples provided herein are illustrative only and not intended to be limiting.

Embodiments of the present disclosure will be described below in detail with reference to the accompanying figures.

Figure 2:
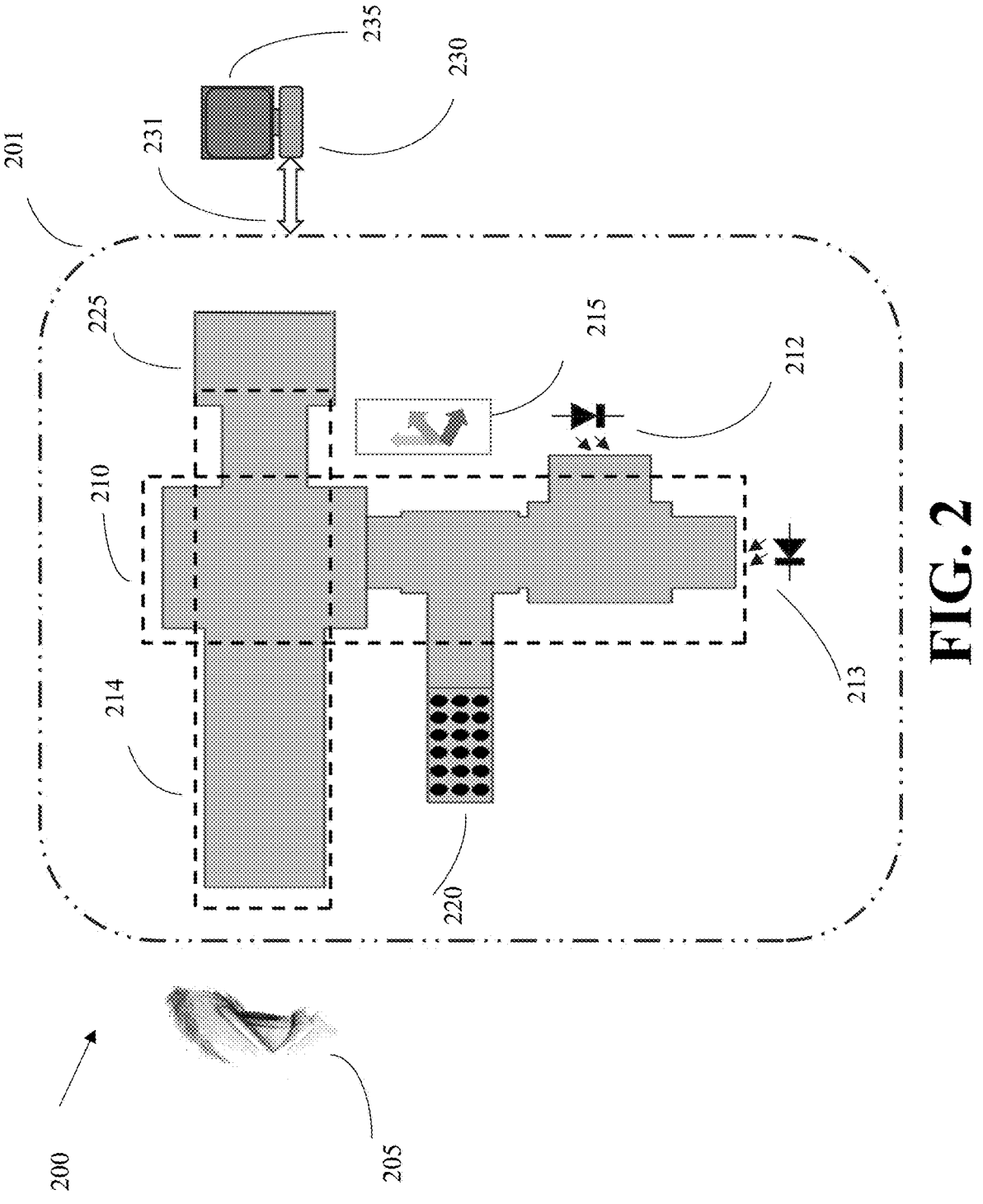
FIG. 2 shows a schematic diagram of an embodiment of the disclosed device.

Embodiments of the present disclosure disclose a System 200 for retinal imaging as shown in FIG. 2. The eye of the subject whose retinal image is to be captured is symbolically shown as 205. The disclosed system 200 comprises a handheld device 201. The handheld device 201 comprises illuminating optics 210, which can be achieved in many ways and hence it is shown enclosed in a dotted line block. The disclosed device also comprises imaging optics 214, which too can be achieved in many ways and hence it is shown enclosed in a dotted line block. The illumination for the eye 205 for imaging is provided by light sources 212 and 213. In one embodiment, the light sources 212 and 213 are Light Emitting Diodes. While other types of light sources may be used, the light weight, low energy consumption, and quick reaction time of LEDs, advantageously LEDs are used in the disclosed device. Hereinafter the light sources are referred to as LED light sources for ease and advantages they provide. Devices similar to the disclosed device using any other sources of light are to be treated as equivalents of the disclosed device.

The light source 212 emits radiation in the Infrared (IR) part of the electromagnetic radiation spectrum (hereinafter, IR LED 212) whereas the LED light source 213 emits radiation in the part of the electromagnetic radiation spectrum that is visible to the human eye (hereinafter, LED 213 or visible light or visible light source). The color of the light emitted by LED 213 could be of any color in the spectrum visible to humans. It could be White, Blue, Amber, Green, Red, for example. In non-mydriatic mode, that is, the pupil of the eye 205 of the subject has not been dilated, for example by topically administering drops of Tropicamide to the ye 205, IR LED 212 is the preferred light source. If subject's pupil, however, has been dilated, LED 213 may emit light of any color, for example, Blue, Amber, Green, Red, etc. White light emitting LED, wherein white is well known to be a combination of all colors, may also be used. Specific colored LEDs may be used for specific purposes like Fundus Fluorescein Angiography or Multispectral imaging, for example. Thus, in the description further, it may be borne in mind that when LED 213 is mentioned, it may be of any color. When the type of image is mentioned, it may also include information on the preferred color of the light emitted by LED 213. Still further LED 213 may be a group of LEDs of different colors and when the computing device conveys a trigger to turn the LED 213 on, it may also include the color of the LED to be turned on. Still further, the whole procedure may be conducted with one LED 213 being used instead of IR LED 212, in the mydriatic mode. However, for the sake of completeness, simplicity, and brevity the use of both LED 212 and LED 213 is mentioned and is non-limiting. The exact configuration of the optics is not relevant here. The image of the eye 205 of the subject is captured by a camera 225. The device 201 comprises a three-dimensional (3-D) accelerometer 215 and a fixation screen 220.

In one embodiment, the positions of the IR LED 212 and LED 13 are interchanged with suitable modifications to the illuminating optics if needed.

Apart from the handheld device 201, the disclosed system 200 comprises a computing device 230 and a display unit 235. The computing device 230 comprises a processor communicatively connected to a memory that stores computer readable modules of instructions that direct the processor to carry out the various functions described hereunder.

The functioning of the device 201 along with the system 200 is described below in sufficient detail to facilitate an understanding of the system and the method behind the functioning of the system 200.

First, the user positions the handheld device 201 in a suitable position such that further operations can begin. For doing this, the user may use the image displayed on the display unit 235. They may also use a viewfinder of the camera (not shown) if the camera has one. However, it may be more convenient to use the display on the display unit 235, which is a larger display than a normal viewfinder. The image data from the camera is communicated to the computing device 230 in a known way using the communication link 231. This position may be referred to as the initial position of the imaging device 200. This positioning is to view the eye of the subject 205 is visible on the screen.

At this stage, the eye 205 of the subject is illuminated using LED light source 212, which produces light in the infrared (IR) range of the spectrum. Since the human eye is not sensitive to IR light, the pupil of the subject's eye does not contract as would happen if the eye 205 were illuminated with visible light. The user then enters or selects the type of image that is required, using the computing device 230. The computing device may display a choice of positions and the user selects one of them or the user types in the required position of the eye. In one embodiment, the different positions may be coded with a number and the user types in only the number using an input device of the computing device, a keyboard for example. Hereinafter only the term "select" is used for both selecting and typing in the name of the required position. Some of the types of images are macula centered, optic disc centered, peripheral up, peripheral down, peripheral left diagonal, peripheral right diagonal, for example.

Depending on the type of image selected by the user, the computing device 230 sends appropriate data to the fixation screen 220. The fixation screen 220 displays the fixation stimulus at the required location. That is to say, one of the dots shown within the fixation screen 220 is turned on, for the subject to focus on. This is referred to as the initial position of the fixation stimulus on the fixation screen (220). Even though the dots are shown as discrete black dots on a white background to facilitate understanding, it may be a set of pixels in between or overlapping the dots shown in the figure and the actual stimulus may be a white or a colored dot on a black or any other dark background, in the fixation screen 220.

The location of the fixation stimulus on the fixation screen 220 could be, for example, for any one of the image types such as macula centered, optic disc centered, peripheral up, peripheral down, peripheral left diagonal, peripheral right diagonal, etc., as well-known in the field of ophthalmology. For the following description, the image type selected by the user will be macula-centered image. For this to happen, the dot at the middle column and middle row of the dots shown in the fixation screen 220 may be activated, such that the subject's eye 205 turns to the right leading to the macula centered image. This is just as an example for the sake of understanding only and should not be treated as limiting in any way.

The position of the fixation stimulus on the fixation screen 220 may be determined by the computing device based on a predetermined algorithm for example. This is a trivial matter and a person skilled in the art to which this disclosure pertains to will be capable of implementing it without difficulty and hence not described herein. Alternatively, a memory associated with the computing device 230 may store predetermined data corresponding to each known type of image that may be selected by the user and convey that data to the fixation screen 220 by the computing device, based on the user selection.

Then, the user directs the subject to focus their gaze on the fixation stimulus for the entire duration of imaging. The term "their" is used above and hereinafter as a singular pronoun instead of using the term "his or her". Once the user has fixed their gaze on the fixation stimulus displayed on the fixation screen 220, the process as per the disclosed method may begin.

The computing device 230 may calculate a new position for the fixation stimulus on the fixation screen (220) in two distinct stages. The first stage may be called artificial intelligence (AI) guided fixation-based stabilization. For this, the computing device 230 performs real time or near real time analysis of the image frames received from the camera 225, by using the optic disc region as reference to obtain the image of the desired region of interest in the captured image. The optic disc is usually the brightest area in these images, as can be seen from the images of FIGS. 1a and 1b, and hence is useful as reference. Using this, the fixation stimulus may be moved to a new position such that the exact desired position of the eye of the subject is reached, in the present example, for a macula-centered image.

Figure 1A:
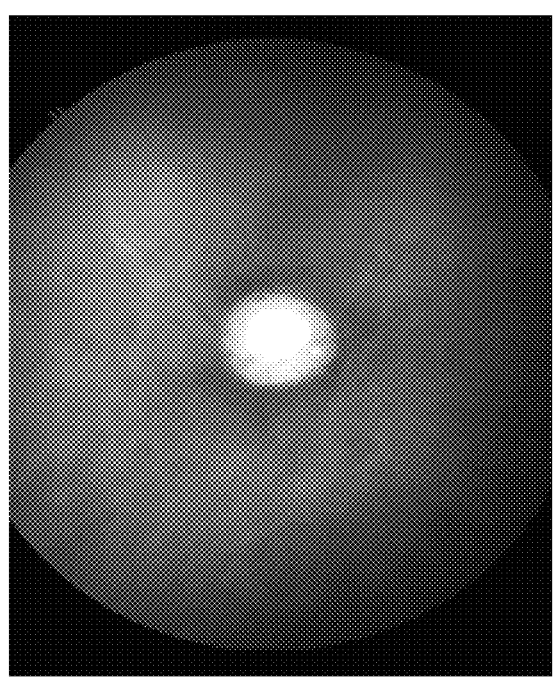
FIGS. 1A and 1B shows examples of two types of retinal images; macula centered and optic disc centered.
Figure 1B:
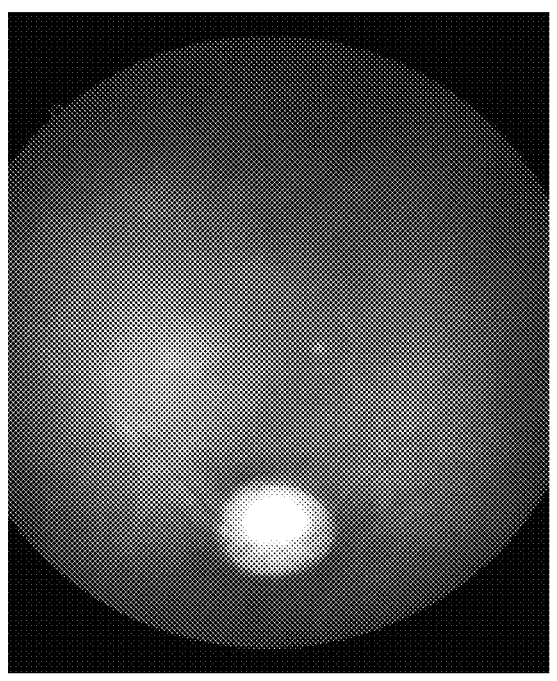

In the second stage, once the desired type of image, say macula-centered image shown in FIG. 1a, using the optic disc as reference is reached; there may be changes in the image due to the movement of the device 201 due to the movement of the hand or hands of the user holding the device 201. The computing device 230 receives data corresponding to the movement of the handheld device 201 from the 3-D accelerometer 215 on the instantaneous spatial location of the device 201. The computing device 230 computes the new position of the device 201 and sends appropriate data on the fixation stimulus on the fixation screen 220 to move it to a new position within the fixation screen 220. This means the fixation stimulus within the fixation screen 220 is displayed at a new point. Image frames of the eye 205 of the subject are captured by the camera 225.

Signals from the 3-D accelerometer 215 and the fixation stimulus position from the fixation screen 220 and the image frames of the eye of the subject 205 captured by camera 225 are conveyed to the computing device 230. The 3-D accelerometer signals are used to calculate a new position for the fixation stimulus on the fixation screen 220 such that it compensates for the motion of the device 200 and continuously ensures that the images captured are always of the required type, in the current example, macula centered image.

As described before, the 3-D accelerometer 215 detects the position of the device 201 in the X, Y, and Z directions and sends the sensor signals to the computing device 230. The computing device 230 processes the signals and transforms the 3-D data to obtain a 2-D equivalent position of the fixation stimulus on the fixation screen 220. If the device 200 moves due to the movement of the hands of the user, the computing device 230 calculates the new coordinates of the device 201 and hence that of the fixation stimulus. This is used by the computing device 230 to achieve fine stabilization by changing the position of the fixation stimulus so that the image of the correct image type is captured. The calculation of a new position for the fixation stimulus on the fixation screen (220) may be carried out using both the image received from the camera 225, using AI techniques, and the 3-D accelerometer 215 simultaneously. It may be described as below.

The expected position for an optic disc is known beforehand depending on the type of image selected by the user. When an image frame is retrieved from camera 225 in real time, the AI technique used checks the current position and compares with desired position. If there is difference in the position, it will guide the fixation stimulus to move left, right, up, or down accordingly on the fixation screen 220. This is a continuous process and applicable as long as the optic disc is visible within the image frame.

This process is continued in real time or near real time as the hand of the user may keep moving. This overall process, AI guided fixation-based stabilization followed by fine stabilization using 3-D accelerometer sensor signals, results in stabilizing the retinal image and capturing the required type of image. The user may manually verify achieving the desired initial position by viewing the image on the display unit 235. The desired position may additionally be verified through the image analysis of frames by the computing device 230, using AI techniques. The position of the eye 205 of the subject, thus achieved may be continuously monitored computing device 230 using the signal from the 3-D accelerometer and stabilize the image continuously. Once the desired position is reached, the camera 225 may be directed by the computing device 230 to capture a still image. Just before the image is captured, the computing device 230 sends a signal to the device 201 to turn the LED 213. In addition, once the LED 213 illuminates the eye with visible light, the computing device issues a trigger to the camera to capture the retinal image with the eye oriented by gazing at the fixation stimulus on the fixation screen 220 to obtain the required type of image, say a macula centered image, through the imaging optics 214.

Even though the illuminating optics and imaging optics are described as different, the illuminating light travels through the imaging optics for at least a part of its path from the LEDs 212 and 213 to the eye (205) of the subject. The two are described herein as separate for ease of understanding.

It is to be noted that the computing device 230 may not use every frame of the video data communicated by the camera 225 since the processing time of the image data from one frame of the video data to determine the new position of the fixation stimulus on the fixation screen 220 may not allow that. Hence, alternate frames of the video data may be used to calculate the new position of the fixation stimulus on the fixation screen 220.

Figure 3A:
FIGS. 3A and 3B shows two types of devices that may be used to create the fixation stimulus described herein.
Figure 3A:
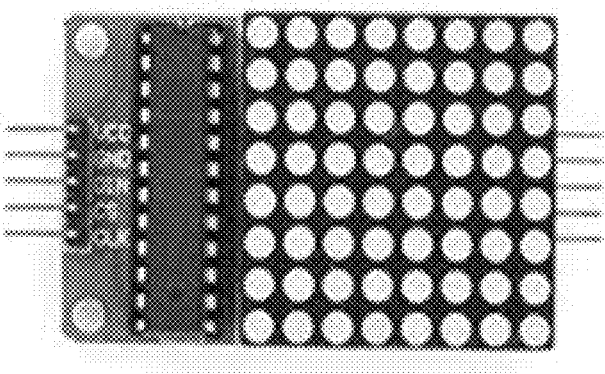
Figure 3B:

The display of the fixation stimulus on the fixation screen 220 may be displayed in more ways than one. FIG. 3 shows two such ways. FIG. 3a is that of a matrix of light emitting diodes and FIG. 3b is a display screen similar to the one used in a mobile phone of any technology, for example. If it is a liquid crystal display (LCD) it may be back lit and the fixation stimulus may be a bright dot that can move, on a black background, based on data from the computing device 230 of FIG. 2, acting as a fixation stimulus. It could also be LED display in which one or more pixels can be lit to form a dot that moves, acting as a fixation stimulus, based on data from the controller 230 of FIG. 2.

Figure 4:
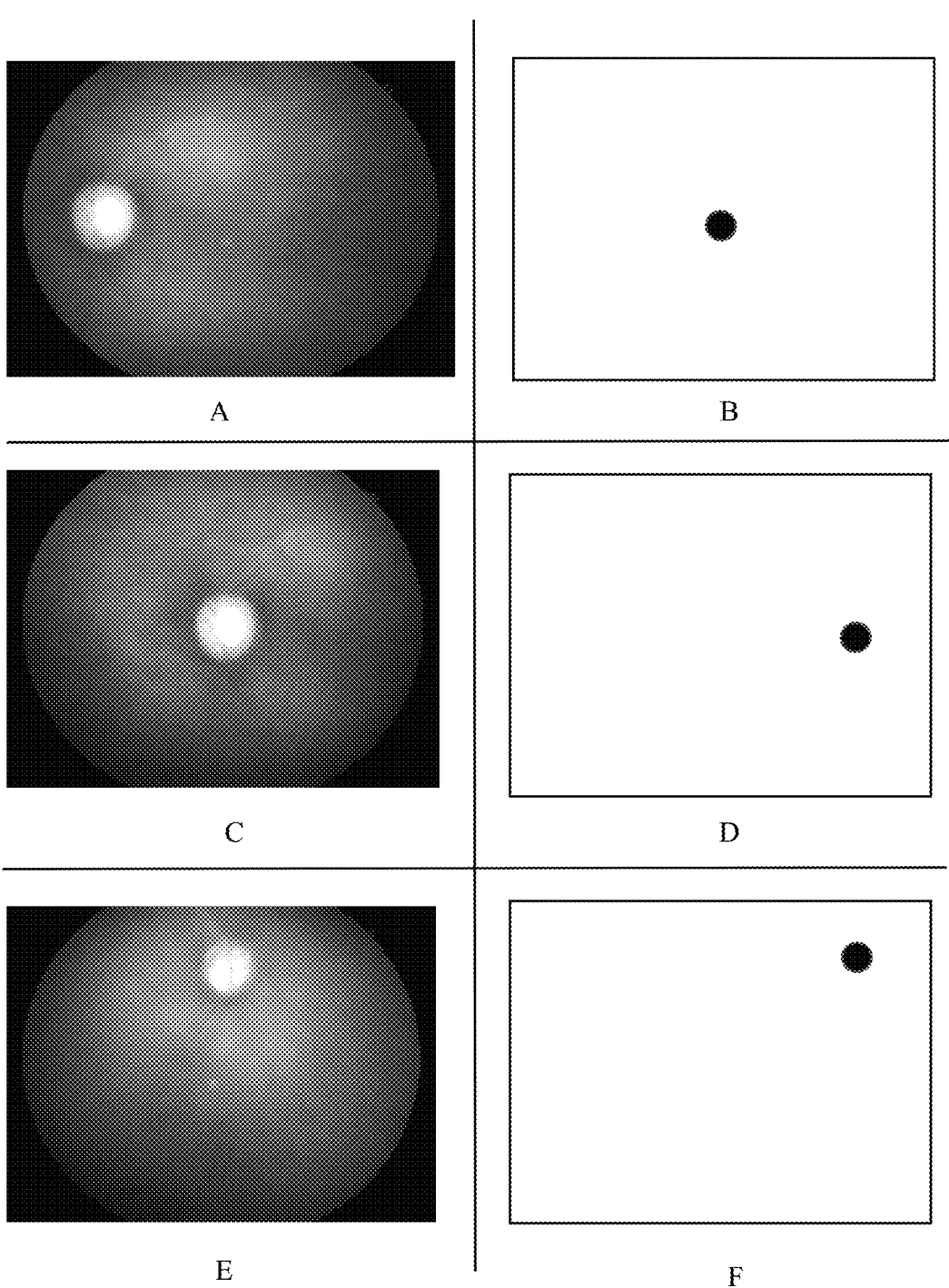
FIG. 4 shows an exemplary way of moving the fixation stimulus for stabilization of the image.

FIG. 4 shows the translation of the optic disc on the image to the location of the fixation on the screen. When the retina is macula centered, with the optic disc to the left as shown in A, the fixation stimulus is centered, as shown in B. In addition, when the retina is optic disc centered C, the fixation stimulus is seen to the right, as shown in D. In E, corresponding to the Peripheral Up position of the optic disc, the fixation stimulus is seen in the top right corner as shown in F. Here, it can be inferred that the fixation is actually translating the position of the macula, which is the dark region on the retina. However, since the optic disc is easily distinguishable, it shall be used to translate the fixation stimulus and as the point of interest for AI analysis of the image frames.

Figure 5:
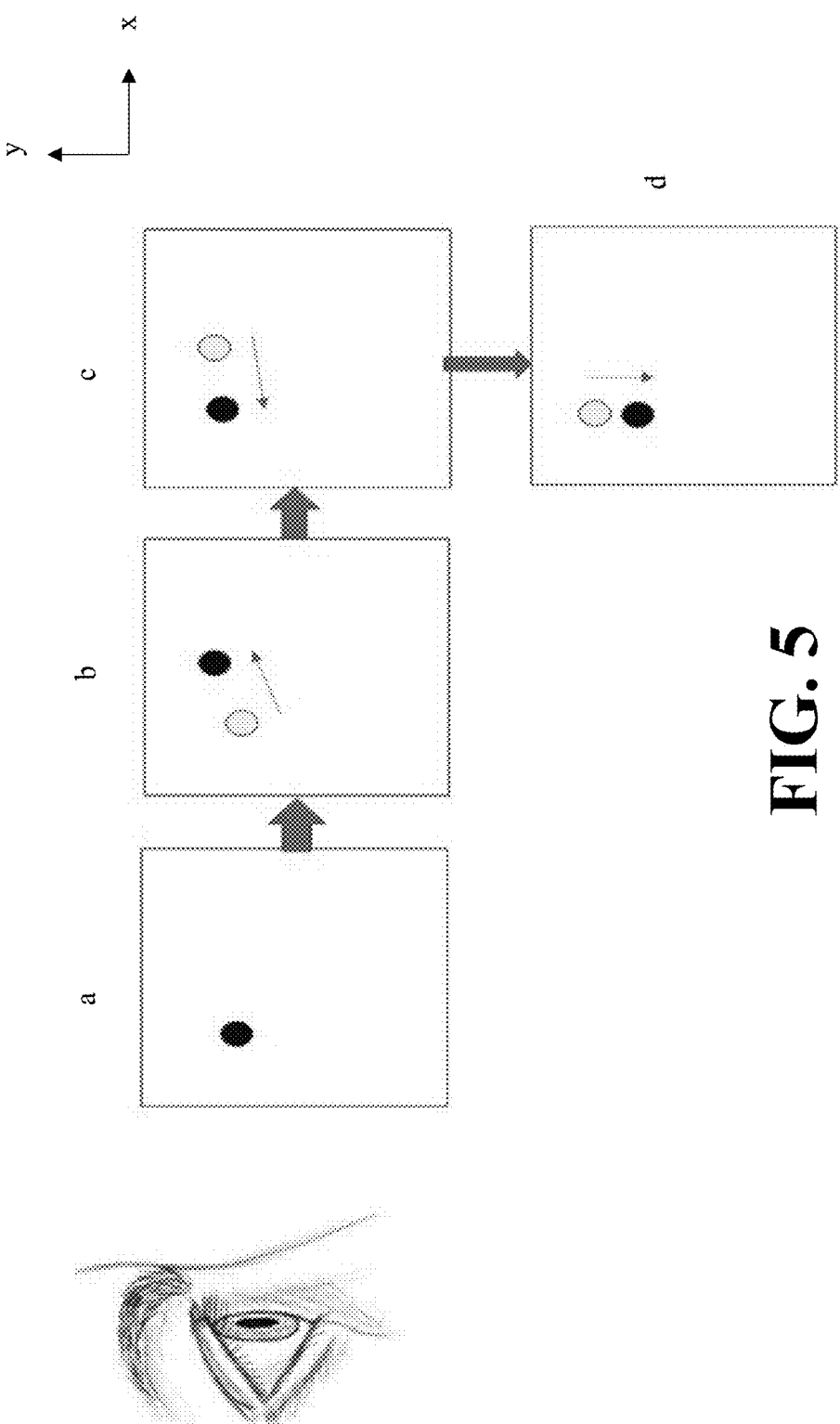
FIG. 5 shows another exemplary way of how the fixation stimulus is moved for stabilization of the image.

FIG. 5 shows, exemplarily, the process of moving the fixation stimulus. In a, the fixation stimulus is shown as a black dot. In b, the dot has moved upward and toward the right. However, it must be noted that the dot has, in fact, remained in the same place with reference to the boundaries the fixation screen 220, but the display unit itself has moved upward and toward the right due to the movement of the device 200. The original position of the dot in 3-D space, with reference to the previous position (not with reference to the boundaries of the fixation screen 220), is shown as grey circle. Using the signal from the 3-D accelerometer and analyzing a current video frame using the disclosed AI technique, the controller 230 of FIG. 2, calculates the new position of the black dot and moves the dot back to original position in space as shown in c. Needless to say, it is now in a different position with reference to the boundaries of the display unit 235 than in a but in such a position as to compensate for the movement of the device 200 such that the eye 205 of the subject is in the correct position for the selected type of image.

The dot in d is commanded to move downward, exemplarily, by the computing device 230, taking into account the type of image needed—macula centered in this example—and carrying out image analysis using AI techniques, the image of the eye 205 of the subject of FIG. 2, imaged by camera 225 of FIG. 2, for example.

The AI technique used herein primarily relies on real time detection of the optic disc, illuminated by either by infrared (IR) light or light visible to the human eye, within the live video frames. This is achieved by the intensity map assessment of each frame, specifically the high intensity region, roughly in the shape of an ellipse.

Stabilization depicted mathematically: Linear Transformation is used to translate the position of the optic disc on the image frame to the position on the fixation screen 220. Using 2-D linear transformations, the translation and the reflection may be calculated.

Translation from one point in 2-D to another point in the same plane:

$$\begin{bmatrix} x' \\ y' \\ 1 \end{bmatrix} = \begin{bmatrix} 1 & 0 & x_0 \\ 0 & 1 & y_0 \\ 0 & 0 & 1 \end{bmatrix} \begin{bmatrix} x \\ y \\ 1 \end{bmatrix} = \begin{bmatrix} x + x_0 \\ y + y_0 \\ 1 \end{bmatrix}$$

Where x0 and y0 are the distances by which the point has shifted in the x and y directions, respectively.

To find the reflection of this point on a plane (the fixation screen 220) that is orthogonal to the image frame, we just multiply it by a transformation matrix. This transformation matrix is a function of the ratio of the size of the image and the size of the fixation screen 220.

optic disc position=(x, y)
fixation position=(x', y')

$$\text{Transformation matrix } (T) = \begin{pmatrix} a & b \\ c & d \end{pmatrix}$$

$$\begin{pmatrix} x' \\ y' \end{pmatrix} = \begin{pmatrix} a & b \\ c & d \end{pmatrix} \begin{pmatrix} x \\ y \end{pmatrix}$$

3-D to 2-D transformation: The movement in the 3-D (x, y, z) space measured using an 3-D accelerometer can be translated to movement in the 2-D (x, y) plane with respect to the fixation using either orthogonal projection which requires just the dropping of the z-axis value or by dividing x and y axis by the z value as shown below.

$$x'=x/z$$

$$y'=y/z$$

The use of AI technique has been mentioned hitherto and a description of the techniques and methods involved as applied to segmentation optic disc (OD) and cropping of the region of interest (RoI) are described below.

The input to the computing device 230 is either an infrared (IR) or RGB color image or a frame from the video captured from the camera 225. The output will be the optic disc (OD) segmented mask wherein the binary image with OD as white and the rest of the image or the areas other than the optic disc as black, with the coordinates of optic disc region in that image/frame.

The following steps are involved in training and using the AI model. The first step is the training phase. It consists of training the U-net model for OD segmentation using the Infra-Red or RGB image/frame and ground truth images consisting of optic disc masks. The U-Net architecture stems from what is generally referred to as "fully convolutional network". The next step is to save the weights of the trained model. The final step is to load the model and use the model for the prediction.

U-net Model is convolutional network architecture for fast and precise segmentation of images. U-net architecture uses skip architectures for fusing fine scale and coarse scale features. The U-net model consists of a contracting path and an expansive path.

The contracting path follows the typical architecture of convolutional neural network. It consists of the following:
Repeated application of (3×3) convolutions
Followed by a batch normalization layer and Rectified linear unit (ReLU) activation and
Dropout and
(2×2) max pooling operation with stride 2 for down sampling.

At each down sampling phase, the model doubles the number of feature channels. The purpose of the contracting path is to capture the context of the input image in order to be able to do segmentation.

The expansive path consists of:
An upsampling of the feature map followed by (2×2) convolution (up-convolution) that halves the number of feature channels,
A concatenation with the corresponding feature map from the contracting path, and
Two (3×3) convolutions, each followed by batch norm, dropout, and a ReLU.

The purpose of this expanding path is to enable precise localization combined with contextual information from the contracting path.

At the final layer, a (1×1) convolution is used to map each component feature vector to the desired number of classes.

The model is trained with fundus images and its corresponding ground truth images. The training phase uses images from REFUGE dataset, a data set of fundus images made available online. The details of an exemplary training dataset are depicted in the table below.

|  | Training (number of images) | Validation (number of images) |
|---|---|---|
| REFUGE | 600 | 200 |
| Other Images from a reliable source | 311 | 100 |

Given below are exemplary details of parameters of

| Height and width of the image | 256 × 256 pixels |
|---|---|
| Loss | Binary cross entropy |
| Optimizer | Adam |
| Metrics | Accuracy |
| Batch size | 16 |
| Number of epochs | 200 (with early stopping condition) |
| Number of training samples | 911 + augmented images |
| Steps per epochs | Number of Train samples/Batch size |

Figure 6:
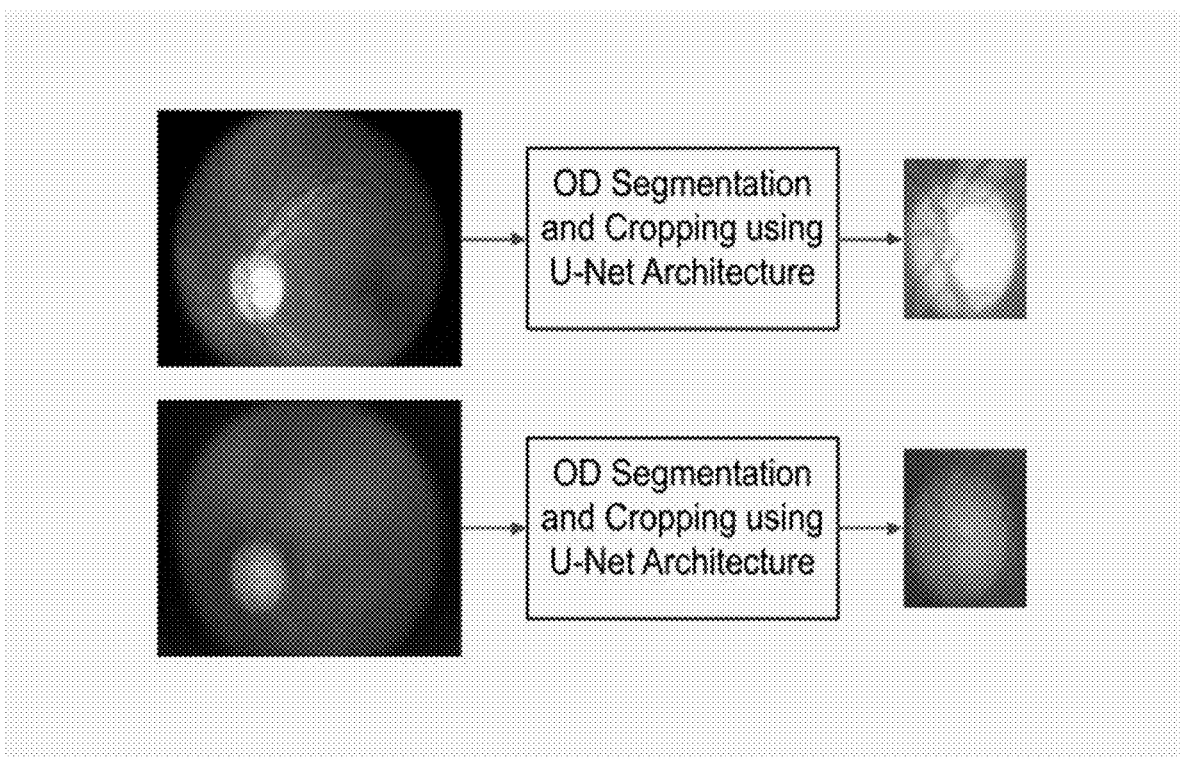
FIG. 6 shows two sets of images showing optic disc segmentation using the disclosed method.

FIG. 6 shows two sets of images showing optic disc segmentation using the disclosed method.

The inventors have realized that the U-net architecture is uniquely suited to solve the present problem this disclosure aims to solve. Those properties are:
Computationally efficient
Trainable with a small dataset
Trained end-to-end—End-to-end learning usually refers to omitting any hand-crafted intermediary algorithms and directly learning the solution of a given problem from the sampled dataset.
Preferable for bio-medical applications The inventors have implemented the disclosed method by training the model using Adam optimizer with learning rate 1.e-4, for optic disc segmentation, using 911 training images, and 300 images for validating the model. The model was tested on 1000 images. Adam optimizer is the extended version of stochastic gradient descent, which could be implemented in various deep learning applications such as computer vision and natural language processing in the future years. The performance was found to be that the optic disc detection using the AI deep learning technique mentioned above provided the coordinates of the optic disc in approximately 100 milliseconds. This performance is suitable for real time or near real time detection of optic disc in an image or a frame of a video provided by the camera 225 and hence well suited for the stabilization mechanism described hitherto.

While hitherto, the retinal imaging device 201 has been described as a part of system wherein the computing device 230 and the display device are external to the retinal imaging device 201, with more and more computational power being available in smaller and smaller devices, a person skilled in the art may advantageously combine them and make the disclosed system as a single device. Such an embodiment is already contemplated by the inventors of this disclosure and it may be treated as a normal or obvious improvement carried out by a person skilled in the art.

Such an embodiment may suffer one disadvantage the display device 235, as described, may be too small for easy operation of the combined device described above. In such a case in one embodiment, the computing device 230 and the retinal imaging device 201 may be combined into a single handheld device and only the display device 235 may be placed outside wherein the computing device 230 communicates image or video data to the external display device 235 for displaying the image or video captured by the camera 225. Such an embodiment is already contemplated by the inventors of this disclosure and may be treated as a normal or obvious improvement carried out by a person skilled in the art.

Figure 7:
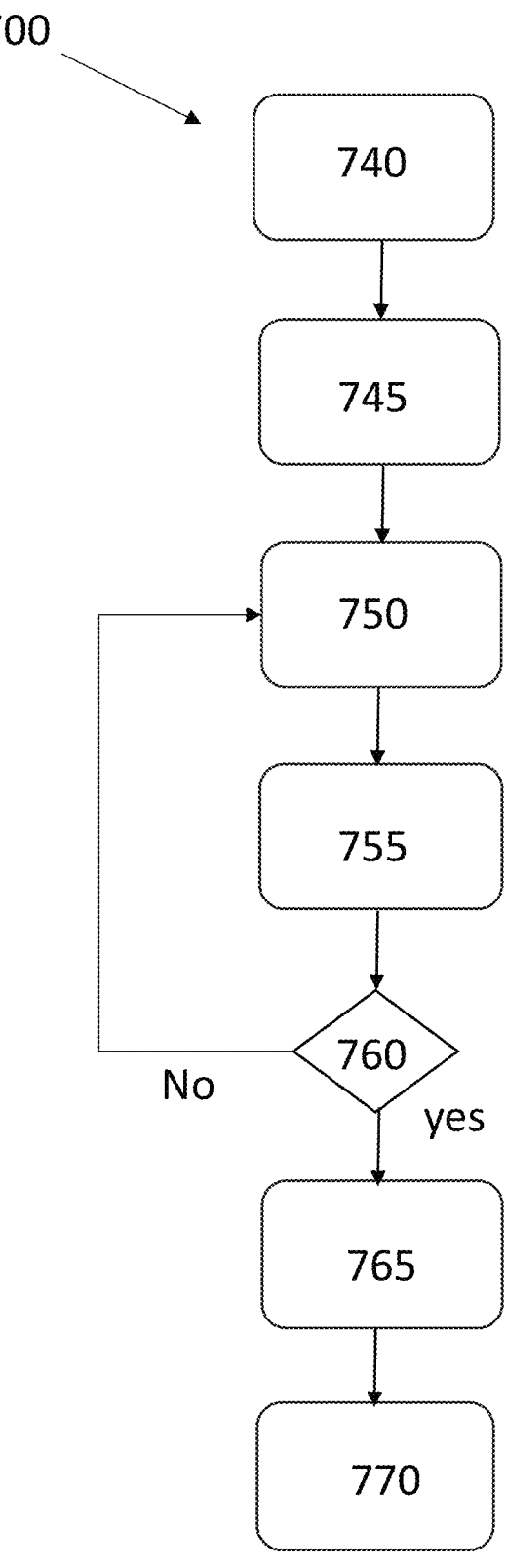
FIG. 7 shows a flow chart of the disclosed method.

Now, the disclosed method 700 will be described in detail with reference to FIG. 7. The method 700 for capturing a stabilized retinal image of an eye 205 of subject, using a handheld retinal-imaging device 201, comprises the following steps. At step 740, the computing device 230 receives a user input on the type of image to be captured. At step 745, the computing device 230 conveys data to the fixation screen 220 in the retinal imaging device 201 on the position of the fixation stimulus on the fixation screen 220.

Then at step 750 the computing device 230 receives video data of the eye 205 of the subject from a camera 225 of the handheld retinal imaging device 201, and data on a position of the handheld retinal imaging device 201, from a 3-D accelerometer 215 of the handheld retinal imaging device 201 and displays the video based on the video data on the display device 235.

At step 755, the computing device 230 calculates a new position for the fixation stimulus on the fixation screen 220 of the handheld retinal imaging device 201, depending on the signal from the 3-D accelerometer 215 and analyzing a current video frame using the disclosed AI technique in order to compensate for the movement of the hand of the user so as to continue getting the required type of image, say a macula centered image.

At step 760, the computing device 230 uses one or more frames of the video data for determining, using artificial intelligence techniques, if a stable image of the eye 205 of the subject is available or not. If such an image is not available, the method repeats steps 750 and 755 and checks if a stable image is available at step 760. These steps repeat until a stable image is obtained.

When the computing device 230 determines that a stable image which is useful is available, at step 765 it conveys a trigger to the light source 213 to turn on and illuminate the eye 205 of the subject and also conveys a trigger to the camera 225 to capturing the stabilized still retinal image of the eye 205 of the subject, that is illuminated by the light source 213.

Finally, at step 770, the computing device 230 displays the stabilized still retinal image on a display device 235 and stores the still image data in a memory of the computing device 230.

While specific language has been used to describe the disclosure, any limitations arising on account of the same are not intended. As would be apparent to a person skilled in the art, various working modifications may be made to the method in order to implement the inventive concept as taught herein.

Figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

We claim:

1. A system to capture a stabilized retinal image of an eye of a subject by a handheld retinal imaging device, the system comprising:

the handheld retinal imaging device; and an external computing device configured to:

receive a user selection from a user, the user selection comprising a type of image to be captured;

convey data on an initial position of a fixation stimulus on a fixation screen based on the user selection;

receive video data of the eye of the subject from a camera and position data from a 3-D accelerometer, and display a video based on the video data received from the camera;

calculate, during the display of the video, an updated two-dimensional position for the fixation stimulus on the fixation screen, wherein to calculate the updated two-dimensional position, the external computing device is configured to:

detect, using artificial intelligence techniques applied to one or more frames of the video, a location of an optic disc relative to a region corresponding to the user-selected type of image; and project movement indicated by the 3-D accelerometer into coordinates of the fixation screen;

dynamically reposition the fixation stimulus on the fixation screen in real time to the updated two-dimensional position to guide the subject's gaze and maintain the user-selected type of image;

determine that a stable image condition is satisfied based on the one or more frames and the position data; and responsive to the stable image condition convey a trigger to a light source of the handheld retinal imaging device for illuminating the eye of the subject for a predefined duration, and convey a trigger to the camera for capturing the stabilized retinal image illuminated by the light source.

2. The system of claim 1, wherein the data on the initial position of the fixation stimulus on the fixation screen is determined by the external computing device based on the user selection and corresponding predetermined data loaded on the external computing device.

3. The system of claim 1, wherein the user selection is a type of image selected from a group of types of images, including macula-centered, optic disc-centered, peripheral up, peripheral down, peripheral left diagonal, and peripheral right diagonal.

4. The system of claim 1, wherein the handheld retinal imaging device comprises:

an infrared light source configured to illuminate the eye of the subject, through illuminating optics configured for illuminating the eye of the subject;

the source of visible light configured to illuminate the eye of the subject, through the illuminating optics, for the predefined duration, based on the trigger received from the external computing device;

the fixation screen configured to display the fixation stimulus for the subject to gaze at during the use of the handheld retinal imaging device, the position of the fixation stimulus on the fixation screen being based on an input received from the external computing device; and the 3-D accelerometer configured to sense data corresponding to a movement of the handheld retinal imaging device and convey it to the external computing device; and the camera configured to:

capture the video data of the eye of the subject and convey the video data to the external computing device; and capture the retinal image of the eye of the subject, based on the trigger received from the external computing device, and convey retinal image data to the external computing device.

5. The system of claim 4, wherein the locations of the infrared light source and the source of visible light are interchanged with corresponding changes to the illuminating optics.

6. A method for capturing a stabilized retinal image of an eye of subject using a handheld retinal imaging device, the method comprising:

a step of receiving, by an external computing device, a user input on a type of image to be captured;

a step of conveying, by the external computing device, data to a fixation screen on an initial position of a fixation stimulus on the fixation screen;

a step of receiving, by the external computing device, video data of the eye of the subject from a camera of the handheld retinal imaging device, and data on a position of the handheld retinal imaging device, from a 3-D accelerometer of the handheld retinal imaging device, and displaying a video based on the video data provided by the camera;

a step of calculating, by the external computing device, during the display of the video, an updated two-dimensional position for the fixation stimulus on the fixation screen by:

a step of detecting, using artificial intelligence techniques applied to one or more frames of the video, a location of an optic disc relative to a region corresponding to the type of image; and a step of projecting movement indicated by the 3-D accelerometer into coordinates of the fixation screen;

a step of dynamically repositioning the fixation stimulus on the fixation screen in real time to the updated two-dimensional position to guide the subject's gaze and maintain the type of image;

a step of determining that a stable image condition is satisfied based on the one or more frames and the position data;

a step of conveying, by the external computing device, in response to the stable image condition, a trigger to a light source to illuminate the eye of the subject for a predefined duration, and conveying a trigger to the camera for capturing the stabilized still retinal image illuminated by the light source; and a step of displaying, by the external computing device, the stabilized retinal image on a display device and storing image data in a memory of the external computing device.

* * * * *